US006896766B2

(12) United States Patent
Sarbo et al.

(10) Patent No.: US 6,896,766 B2
(45) Date of Patent: May 24, 2005

(54) PAPER WIPING PRODUCTS TREATED WITH A HYDROPHOBIC ADDITIVE

(75) Inventors: Benjamin Sarbo, Winneconne, WI (US); Lisa A. Flugge, Neenah, WI (US); Matthew Higgins, Neenah, WI (US); Jeff Loritz, Appleton, WI (US); Bozena Nogaj, Appleton, WI (US); Mary Philip, Oshkosh, WI (US); Darnell Radtke, Shiocton, WI (US); Thomas G. Shannon, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 48 days.

(21) Appl. No.: 10/325,493

(22) Filed: Dec. 20, 2002

(65) Prior Publication Data

US 2004/0118532 A1 Jun. 24, 2004

(51) Int. Cl.$^7$ ........................ D21H 21/16; D21H 23/70; D21H 19/68; D21H 19/84; D21H 27/30
(52) U.S. Cl. ........................ 162/112; 162/135; 162/158; 162/134; 162/161; 162/179; 428/340; 428/153; 428/537.5; 424/402
(58) Field of Search ........................ 162/109, 111–113, 162/117, 134–135, 158, 169, 164.1, 168.1, 161, 123–128, 179; 428/340–341, 153–154, 537.5; 424/400–401; 427/361, 391; 156/183

(56) References Cited

U.S. PATENT DOCUMENTS

| | | |
|---|---|---|
| 3,203,823 A | 8/1965 | Grimes |
| 3,556,932 A | 1/1971 | Coscia et al. |
| 3,556,933 A | 1/1971 | Williams et al. |
| 3,700,623 A | 10/1972 | Keim |
| 3,772,076 A | 11/1973 | Keim |
| 3,814,096 A | 6/1974 | Weiss et al. |
| 3,855,158 A | 12/1974 | Petrovich et al. |
| 3,879,257 A | 4/1975 | Gentile et al. |
| 3,899,388 A | 8/1975 | Petrovich et al. |
| 4,129,528 A | 12/1978 | Petrovich et al. |
| 4,147,586 A | 4/1979 | Petrovich et al. |
| 4,222,921 A | 9/1980 | Van Eenam |
| 4,357,827 A | 11/1982 | McConnell |
| 4,426,418 A | 1/1984 | Coleman et al. |
| 4,481,243 A | 11/1984 | Allen |
| 4,513,051 A | 4/1985 | Lavash |
| 4,514,345 A | 4/1985 | Johnson et al. |
| 4,528,239 A | 7/1985 | Trokhan |
| 4,672,893 A | 6/1987 | Mammarella, Sr. |
| 4,683,001 A | 7/1987 | Floyd et al. |
| 5,048,589 A | 9/1991 | Cook et al. |
| 5,098,522 A | 3/1992 | Smurkoski et al. |
| 5,129,988 A | 7/1992 | Farrington, Jr. |
| 5,209,953 A | 5/1993 | Grupe et al. |
| 5,215,626 A | 6/1993 | Ampulski et al. |
| 5,227,242 A | 7/1993 | Walter et al. |
| 5,230,776 A | 7/1993 | Andersson et al. |
| 5,246,545 A | 9/1993 | Ampulski et al. |
| 5,246,546 A | 9/1993 | Ampulski |
| 5,250,171 A | 10/1993 | Warburton et al. |
| 5,275,700 A | 1/1994 | Trokhan |
| 5,328,565 A | 7/1994 | Rasch et al. |
| 5,334,286 A | 8/1994 | Van Phan et al. |
| 5,334,289 A | 8/1994 | Trokhan et al. |
| 5,353,521 A | 10/1994 | Orloff |
| 5,385,642 A | 1/1995 | Van Phan et al. |
| 5,385,643 A | 1/1995 | Ampulski |
| 5,399,412 A | 3/1995 | Sudall et al. |
| 5,431,786 A | 7/1995 | Rasch et al. |
| 5,494,554 A | 2/1996 | Edwards et al. |
| 5,496,624 A | 3/1996 | Stelljes, Jr. et al. |
| 5,500,277 A | 3/1996 | Trokhan et al. |
| 5,514,523 A | 5/1996 | Trokhan et al. |
| 5,525,345 A | 6/1996 | Warner et al. ............... 424/402 |
| 5,554,467 A | 9/1996 | Trokhan et al. |
| 5,558,873 A | 9/1996 | Funk et al. |
| 5,566,724 A | 10/1996 | Trokhan et al. |
| 5,598,642 A | 2/1997 | Orloff et al. |
| 5,601,871 A | 2/1997 | Krzysik et al. |
| 5,614,293 A | 3/1997 | Krzysik et al. |
| 5,624,790 A | 4/1997 | Trokhan et al. |

(Continued)

FOREIGN PATENT DOCUMENTS

| | | | |
|---|---|---|---|
| EP | 0283405 A1 | 9/1988 | |
| EP | 792144 B1 | 12/1998 | .......... A47K/00/00 |
| EP | 1005858 A1 | 6/2000 | |
| EP | 1104821 A1 | 6/2001 | |
| WO | WO 9614835 A1 | 5/1996 | |

(Continued)

OTHER PUBLICATIONS

Abstract of Japanese Patent No. 04256721, Sep. 11, 1992.

PCT Search Report, Mar. 16, 2004.

*Primary Examiner*—José A. Fortuna
(74) *Attorney, Agent, or Firm*—Dority & Manning, P.A.

(57) ABSTRACT

Paper products treated on two surfaces with a liquid resistant composition are disclosed. The paper products can be, for instance, bath tissues, facial tissues, paper towels, and industrial wipers. The liquid resistant compositions can include any additive that provides benefits to the product. For instance, the liquid resistant composition can be a softener containing a hydrophobic additive. In one embodiment, the hydrophobic additive is a polysiloxane. In accordance with the present invention, the water resistant composition is applied to each surface according to a pattern. Each of the patterns includes treated and untreated areas. The patterns are positioned on the paper product such that untreated areas on one surface are in correspondence with the treated areas on the other surface of the sheet.

63 Claims, 3 Drawing Sheets

U.S. PATENT DOCUMENTS

| | | | |
|---|---|---|---|
| 5,628,876 A | 5/1997 | Ayers et al. | |
| 5,665,426 A | 9/1997 | Krzysik et al. | |
| 5,705,164 A | 1/1998 | Mackey et al. | 424/400 |
| 5,716,692 A | 2/1998 | Warner et al. | |
| 5,756,112 A | 5/1998 | Mackey | |
| 5,814,188 A | 9/1998 | Vinson et al. | |
| 5,869,075 A | 2/1999 | Krzysik | |
| 5,885,697 A | 3/1999 | Krzysik et al. | |
| 5,914,177 A | 6/1999 | Smith, III et al. | |
| 6,007,627 A | 12/1999 | Barnholtz | |
| 6,054,020 A | 4/2000 | Goulet et al. | |
| 6,096,169 A | 8/2000 | Hermans et al. | |
| 6,126,784 A | 10/2000 | Ficke et al. | 162/184 |
| 6,129,815 A | 10/2000 | Larson et al. | |
| 6,143,135 A | 11/2000 | Hada et al. | |
| 6,168,852 B1 | 1/2001 | Smith, III et al. | |
| 6,179,961 B1 | 1/2001 | Ficke et al. | |
| 6,187,695 B1 | 2/2001 | Krzysik et al. | |
| 6,214,146 B1 | 4/2001 | Merker | 156/183 |
| 6,217,707 B1 | 4/2001 | Garvey et al. | |
| 6,224,714 B1 | 5/2001 | Schroeder et al. | |
| 6,231,719 B1 | 5/2001 | Garvey et al. | |
| 6,261,580 B1 | 7/2001 | Lehrter et al. | |
| 6,270,878 B1 | 8/2001 | Wegele et al. | |
| 6,274,667 B1 | 8/2001 | Shannon et al. | |
| 6,277,241 B1 | 8/2001 | Merker et al. | 162/111 |
| 6,287,418 B1 | 9/2001 | Schroeder et al. | |
| 6,332,952 B1 | 12/2001 | Hsu et al. | |
| 6,365,667 B1 | 4/2002 | Shannon et al. | |
| 6,428,794 B1 | 8/2002 | Klofta et al. | 424/401 |
| 6,500,289 B2 | 12/2002 | Merker et al. | 156/183 |
| 6,534,151 B2 | 3/2003 | Merker | 428/154 |
| 6,541,099 B1 | 4/2003 | Merker et al. | 428/194 |
| 2001/0015251 A1 | 8/2001 | Merker | 156/183 |
| 2002/0062911 A1 | 5/2002 | Merker et al. | 156/183 |
| 2002/0084048 A1 | 7/2002 | Merker et al. | 162/123 |
| 2003/0077314 A1 | 4/2003 | Shannon et al. | 424/443 |
| 2004/0031578 A1 * | 2/2004 | Tirimacco | 162/111 |

FOREIGN PATENT DOCUMENTS

| | | | |
|---|---|---|---|
| WO | WO 9846825 A1 * | 10/1998 | D21F/11/14 |
| WO | WO 9906634 A1 | 2/1999 | |
| WO | WO 9920821 A1 | 4/1999 | D04H/1/46 |
| WO | WO 9925924 A1 | 5/1999 | D21H/27/38 |
| WO | WO 0000698 A1 | 1/2000 | |
| WO | WO 0004233 A1 | 1/2000 | |
| WO | WO 0048544 A1 | 8/2000 | |
| WO | WO 0064407 A1 | 11/2000 | |
| WO | WO 200100141 A1 | 1/2001 | A61K/00/00 |
| WO | WO 0148312 A1 | 7/2001 | |
| WO | WO 0149933 A2 | 7/2001 | |
| WO | WO 200148312 A1 | 7/2001 | B32B/9/04 |
| WO | WO 200149933 A2 | 7/2001 | A41D/31/00 |
| WO | WO 2003021037 A1 | 3/2003 | A61K/9/70 |

* cited by examiner

PAPER WIPING PRODUCTS TREATED WITH A HYDROPHOBIC ADDITIVE

BACKGROUND OF THE INVENTION

Consumers use paper products, such as facial tissues, bath tissues, and paper towels, for a wide variety of applications. Facial tissues are not only used for nose care but, in addition to other uses, can also be used as a general wiping product. Consequently, there are many different types of tissue products currently commercially available.

In some applications, paper products are treated with lotions and/or various other additives for numerous desired benefits. For example, formulations containing polysiloxanes have been topically applied to tissue products in order to increase the softness of the product. In particular, adding silicone compositions to a facial tissue can impart improved softness to the tissue while maintaining the tissue's strength.

Some chemical additives, such as various softening agents including polysiloxanes, can have a tendency to impart hydrophobicity to the treated paper web. Increasing the hydrophobicity of a tissue product can provide various benefits and advantages. For example, treating the outside surfaces of a tissue product with a hydrophobic additive tends to trap liquids absorbed by the product within the internal space of the product thus preventing the liquids from flowing through the product. Consequently, fluids that are absorbed by the tissue product during use tend to remain captured within the product.

Although hydrophobicity can be desired in some applications, increased hydrophobicity can adversely affect the product. For instance, increased hydrophobicity in a paper product, such as a tissue, can adversely impact upon the ability of the wiping product to absorb liquids. Hydrophobic agents can also prevent bath tissue from being wetted in a sufficient amount of time and prevent disintegration and dispersing when disposed in a commode or toilet. Hence, additives that are hydrophobic in nature can make it difficult to find a proper balance between improving the properties of a web through the use of the additive and yet maintaining acceptable absorbency and wetability characteristics.

Thus, a need currently exists for a process of applying water resistant chemical additives, particularly hydrophobic compositions, to paper products for providing benefits to the product without increasing the hydrophobicity of the product beyond desirable limits.

SUMMARY OF THE INVENTION

In general, the present invention is directed to paper products that have been treated with a water resistant chemical composition for improving the properties of the product while maintaining acceptable wetability properties. As used herein, the phrase "water resistant" simply means that the composition inhibits liquids from being absorbed by the paper product. For instance, in one embodiment, the present invention is directed to a tissue product having a first side and a second side. The tissue product can have a bulk density of at least about 2 cc/g, such as at least about 3 cc/g and can have a basis weight of from about 6 gsm to about 150 gsm. In addition, the tissue product can be a multi-ply product.

In accordance with the present invention, a water resistant additive, such as a hydrophobic additive is applied, in this embodiment, to the first side of the tissue sheet according to a first pattern and applied to the second side of the tissue sheet according to a second pattern. The first pattern and the second pattern cover from about 50% to about 99% of the coated surface area of each side of the sheet. As used herein, the "coated" surface area of a sheet is the portion of the sheet where the pattern is located. For instance, the pattern can cover an entire side of a sheet or it can be located in a particular area. For example, in one embodiment, the pattern can appear in the middle region of the sheet surrounded by an untreated perimeter area.

Each of the patterns includes non-treated areas and treated areas. The first pattern may be identical to the second pattern, or can be different. The patterns are applied to the tissue sheet in an offset relationship such that the non-treated areas applied to one side of the tissue sheet are located opposite treated areas on the other side of the tissue sheet. In this manner, a tissue product can be made having good wetability properties even when treated with a hydrophobic composition. Further, it has been discovered that through the process of the present invention the fluid strikethrough properties of the product can also be controlled.

Fluid strikethrough refers to the ability of the fluid being absorbed to pass from one side of the sheet to the other side of the sheet. While tissue products are expected to be absorbent, it is desirable that such tissue products prevent the passage of the fluid from contacting the user's hand. The ability of a tissue sheet to absorb fluids quickly can be measured by its wet out time described hereinafter. The strikethrough property of the tissue can be measured using the Hercules Size Test (HST) also described hereinafter.

For instance, in one embodiment of the present invention, a tissue product can be formed having a wet out time of no greater than about 15 seconds, particularly no greater than about 12 seconds, and more particularly no greater than about 10 seconds. Even with the above wetability properties, the tissue product can also have a fluid strikethrough such that the product has a Hercules Size Test result of at least about 0.5 seconds, particularly at least about 1.0 seconds.

The patterns that are used to apply the water resistant chemical additive to each side of the paper sheet can vary depending upon the particular application. For example, in one embodiment, the treated areas and untreated areas can form alternating columns on each side of the paper sheet. Alternatively, the untreated areas can comprise pockets surrounded on all sides by the treated areas. The pockets can have any particular shape and can be arranged randomly across the sheet or according to a particular pattern, such as in columns.

In one particular embodiment of the present invention, the first and second patterns comprise alternating stripes. A first set of stripes can comprise columns completely covered by the water resistant chemical additive. Each pattern can also contain a second set of stripes comprising columns having treated areas and untreated areas. The treated areas can form, for instance, a grid within the untreated areas.

In general, any suitable water resistant chemical additive can be applied according to the present invention. Such additives can include, for instance, a softener, a lotion, a skin-conditioning agent, a sunscreen agent, an anti-acne agent, an anti-microbial agent, a cosmetic astringent, an emollient, and mixtures thereof. In one embodiment, the hydrophobic agent can be selected from surface sizing agents known to those skilled in the art. These sizing agents are added to the tissue to primarily enhance the hydrophobic properties of the tissue sheet. In another particular embodiment, for instance, the water resistant chemical additive is a hydrophobic softener. In particular, the hydrophobic softener can be a silicone, such as a polysiloxane. Polysiloxanes are used primarily as softeners and anti-friction agents.

The manner in which the water resistant additive is topically applied to the paper product in accordance with the present invention is generally not critical. For example, the additive can be applied using a gravure printer, an inkjet printer, or a flexographic printer.

The paper product can be any suitable tissue product, such as a paper towel, a wiper, a bath tissue, a facial tissue and the like. While the current invention is applicable to any paper sheet, the process of the present invention is particularly well suited for use in conjunction with paper tissue and towel products. Paper tissue and towel products as used herein are differentiated from other paper products in terms of their bulk. The bulk of the products of this invention is calculated as the quotient of the caliper (hereinafter defined), express in microns, divided by the basis weight, expressed in grams per square meter. The resulting bulk is expressed as cubic centimeters per gram. Writing papers, newsprint and other such papers have higher strength, stiffness, and density (low bulk) in comparison to tissue products which tend to have much higher calipers for a given basis weight. The tissue products of the present invention have a bulk greater than 2 $g/cm^3$, more preferably greater than 2.5 $g/cm^3$ and still more preferably greater than about 3 $g/cm^3$.

The caliper as used herein is the thickness of a single sheet and can either be measured as the thickness of a single sheet or as the thickness of a stock of ten sheets and dividing the ten sheet thickness by ten, where each sheet within the stack is placed with the same side up. Caliper is expressed in microns. It is measured in accordance with TAPPI test methods T402 'Standard Conditioning and Testing Atmosphere For Paper, Board, Pulp Handsheets and Related Products" and T411 om-89 "Thickness (caliper) of Paper, Paperboard, and Combined Board" optionally with Note 3 for stacked sheets. The micrometer used for carrying out T411 om-89 is a Bulk Micrometer (TMI Model 49-72-00, Amityville, N.Y.) or equivalent having an anvil diameter of 4$\frac{1}{16}$ inches (103.2 millimeters) and an anvil pressure of 220 grams/square inch (3.3 kilo Pascals).

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figure in which.

Figure 1:
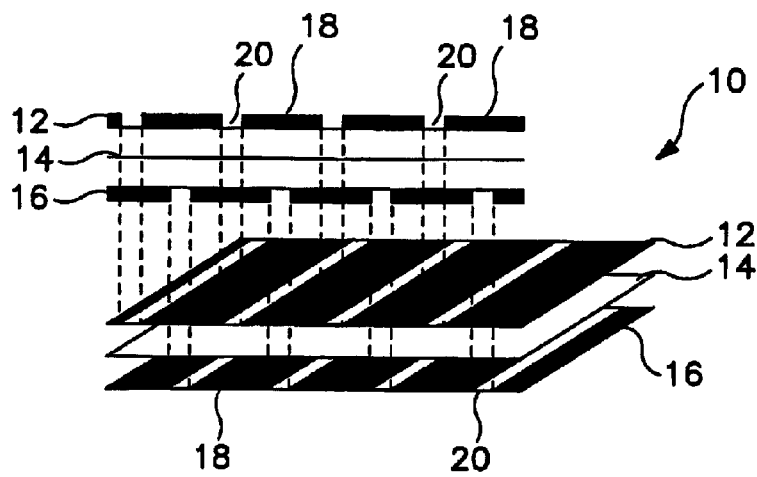
FIG. 1 is a perspective view of one embodiment of a multi-ply tissue product made in accordance with the present invention.

Repeat use of reference characters in the present specification and drawings is intended to represent same or analogous features or elements of the present invention.

DETAILED DESCRIPTION

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents.

The present invention is generally directed to paper products that have been topically treated with a hydrophobic or water resistant composition, such as a composition containing a hydrophobic additive. For example, in one embodiment, the composition can comprise a polysiloxane.

In accordance with the present invention, the water resistant composition is applied to both sides of a paper product in a manner that minimizes fluid intake time while maintaining softness. In particular, the water resistant composition may be applied to each side of the paper product in a pattern that includes treated areas and untreated areas on the product. The patterns are arranged on each side of the paper product in an offset manner. Consequently, fluids coming into contact with the paper product can be easily absorbed due to the presence of the untreated areas. Further, since the patterns are offset, fluids will be absorbed by the paper product without substantially traveling directly through the product. Ultimately, paper products made according to the present invention have a fast initial fluid intake, yet a delayed fluid strike through.

The present invention is particularly well suited for use in conjunction with tissue products, such as paper towels, industrial wipers, bath tissue, facial tissue, and the like. The paper product can be a single ply product or, alternatively, a multi-ply product. For example, in one embodiment, the paper product is a three-ply facial tissue.

In a particular embodiment the tissue product is a multi-ply tissue product comprising three or more plies and comprising a first exterior ply, a second exterior ply and one or more internal plies. The hydrophobic additive is applied to the exterior surfaces of the first and second exterior plies in the aforementioned offset pattern. The internal plies of the tissue sheet are substantially free of the hydrophobic additive resulting in a tissue sheet with ability to absorb fluids quickly while having improved strikethrough properties.

The patterns that are used to apply the water resistant composition to the paper product can vary depending upon the particular application and the desired results. For example, such factors to consider are the type of additive being applied to the paper product, the physical properties of the additive, the amount of untreated space needed on the paper product, the manner in which the additive is being applied to the paper product, and the type of paper product being treated. For example, the resistant composition can be applied to the paper product in offset uniform stripes, offset uniform and zoned stripes, patterns containing untreated pockets or untreated discrete areas, and the like. In accordance with the present invention, the same pattern can be applied to each side of the paper product in an offset relationship or, alternatively, different patterns can be applied to each side of the product.

Various different types of compositions can be applied to paper webs in accordance with the present invention. Possible ingredients in a water resistant chemical additive that can be applied to paper webs in accordance with the present invention include, without limitation, debonders, anti-acne actives, antimicrobial actives, antifungal actives, antiseptic actives, antioxidants, cosmetic astringents, drug astringents, biological additives, deodorants, emollients, external analgesics, film formers, fragrances, and other skin moisturizing ingredients known in the art, opacifiers, skin conditioning agents, skin exfoliating agents, skin protectants, solvents, sunscreens, and surfactants. The above chemical additives can be applied alone or in combination with other additives in accordance with the present invention.

In one embodiment of the present invention, the process is directed to applying a softener to a tissue web. The softener can be, for instance, a polysiloxane that makes a tissue product feel softer to the skin of a user.

Polysiloxanes encompass a very broad class of compounds. They are characterized in having a backbone structure:

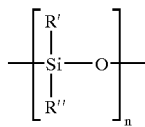

wherein R' and R" can be a broad range of organo and non-organo groups including mixtures of such groups and where n is an integer greater than 2. These polysiloxanes may be linear, branched or cyclic. They include a wide variety of polysiloxane copolymers containing various compositions of functional groups, hence, R' and R" actually may represent many different types of groups within the same polymer molecule. The organo or non-organo groups may be capable of reacting with cellulose to covalently, ionically or hydrogen bond the polysiloxane to the cellulose. These functional groups may also be capable of reacting with themselves to form crosslinked matrixes with the cellulose. The scope of the invention should not be construed as limited by a particular polysiloxane structure so long as that polysiloxane structure delivers the aforementioned product or process benefits, that is, the ability to deliver a degree of hydrophobicity to the tissue sheet.

While not wishing to be bound by theory, when used for softness, the softness benefits that polysiloxanes deliver to cellulose containing products is believed to be, in part, related to the molecular weight of the polysiloxane. Viscosity is often used as an indication of molecular weight of the polysiloxane as exact number or weight average molecular weights are often difficult to determine. In various embodiments of the present invention where the intent is to deliver softness through use of the polysiloxane, the viscosity of the polysiloxanes is greater than about 25 centipoise, in another embodiment greater than 50 centipoise and in still another embodiment greater than 100 centipoise. Viscosity as referred to herein refers to the viscosity of the neat polysiloxane itself and not to the viscosity of an emulsion if so delivered. It should also be understood that the polysiloxanes of the current invention may be delivered as solutions containing diluents. Such diluents may lower the viscosity of the solution below the limitations set above, however, the efficacious part of the polysiloxane should conform to the viscosity ranges given above. Examples of such diluents include but are not limited to oligomeric and cyclo-oligomeric polysiloxanes such as octamethylcyclotetrasiloxane, octamethyltrisiloxane, decamethylcyclopentasiloxane, decamethyltetrasiloxane and the like including mixtures of said compounds.

A specific class of polysiloxanes suitable for the invention has the general formula:

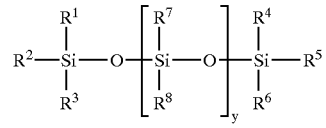

wherein the $R^1$–$R^8$ moieties can be independently any organofunctional group including $C_1$ or higher alkyl groups, ethers, polyethers, polyesters, amines, imines, amides, or other functional groups including the alkyl and alkenyl analogues of such groups and y is an integer >1. Preferably the $R^1$–$R^8$ moieties are independently any $C_1$ or higher alkyl group including mixtures of said alkyl groups. Exemplary fluids are the DC-200 fluid series, manufactured and sold by Dow Corning, Inc.

In one embodiment, the polysiloxane is chosen from the group of so called "amino functional" functional polysiloxanes of the general formula:

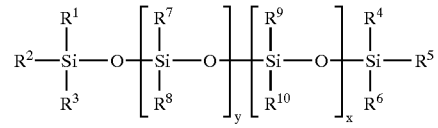

wherein x and y are integers >0. The mole ratio of x to (x+y) can be from about 0.005 percent to about 25 percent. The $R^1$–$R^9$ moieties can be independently any organofunctional group including $C_1$ or higher alkyl groups, ethers, polyethers, polyesters, amines, imines, amides, or other functional groups including the alkyl and alkenyl analogues of such groups. The $R^{10}$ moiety is an amino functional moiety including but not limited to primary amine, secondary amine, tertiary amines, quaternary amines, unsubstituted amides and mixtures thereof. An exemplary $R^{10}$ moiety contains one amine group per constituent or two or more amine groups per substituent, separated by a linear or branched alkyl chain of $C_1$ or greater. An exemplary material includes but is not limited to 2-8220 fluid manufactured and sold by Dow Corning.

Use of amino functional polysiloxanes as a topical treatment to improve the softness of tissue is broadly known in the art. The amino functional polysiloxanes tend to deliver superior softness relative to non-derivatized polysiloxanes and other derivatized polysiloxanes such as ethoxylated polysiloxanes having significant hydrophilic character. While the amino functional polysiloxanes are preferred for delivering superior softness they also tend to deliver significantly higher levels of hydrophobicity to the treated products. Some commercially available examples of polysiloxanes include, AF-21, AF-23 and EXP-2025G of Kelmar Industries, Duncan, S.C., Y-14128, Y-14344, and Y-14461 of the Crompton Corporation, Greenwich, Conn., and Dow Corning 8620, Dow Corning 2-8182, Dow Corning 2-8220, and Dow Corning 2-8194 of the Dow Corning Corporation, Midland, Mich.

As explained above, polysiloxanes and other additives were used sparingly in some applications due to their hydrophobicity. For, instance, problems have been experienced in applying polysiloxane softeners to bath tissue due to the adverse impact upon the wetability of the tissue. By applying the polysiloxanes according to the present invention it has been discovered that water resistant compositions, such as hydrophobic compositions, can be applied to tissue webs for improving the properties of the webs while maintaining acceptable wetability properties.

The water resistant chemical compositions are applied to each side of the paper product according to patterns of treated areas and untreated areas that are spaced in an offset relationship. The phrase "offset relationship" as used in this application means that untreated areas on one side of the paper product are substantially overlapped by treated areas on the opposite side of the paper product.

As described above, the pattern applied to one side of the paper product can be the same or different than the pattern applied to the opposite side of the paper product. In general, the patterns can be applied to the paper product such that the water resistant composition covers from about 50% to about 99.9% of the coated surface area of one side of the paper web. For instance, in one embodiment, each pattern can cover at least about 80% of the surface area of one side of the sheet, and, in another embodiment can cover at least about 90% of the surface area of one side of the sheet.

Referring to FIGS. 1–7, various embodiments of the present invention are illustrated. For instance, one embodiment of the present invention is illustrated in FIG. 1. FIG. 1 is a three-dimensional representation of a paper product 10 including a top ply 12, a middle ply 14, and a bottom ply 16. Paper product 10 can be any suitable wiping product, such as a paper towel, a wiper, a bath tissue, a facial tissue, and the like. In accordance with the present invention, plies 12 and 16 have been treated with a water resistant composition. As shown, the paper product 10 includes treated areas 18 where the water resistant composition has been applied and untreated areas 20. As shown, the water resistant composition is applied to plies 12 and 16, while middle ply 14 remains untreated.

FIG. 1 shows treated areas 18 and untreated areas 20 forming alternating columns on each side of the paper sheet. In this particular embodiment of the present invention, 100% of the non-treated areas of the first side of the product can be opposite treated areas of the second side of the product. In this manner, liquids contacting the paper product 10 are quickly absorbed due to the presence of the untreated areas 20. Further, since the untreated areas 20 are located opposite treated areas, any fluids absorbed by the paper product are held within the center of the product and are inhibited from striking through the product to the opposite side.

Although the paper product 10 as shown in FIG. 1 includes three plies, it should be understood that product 10 can be a single ply product, can be a two-ply product, or can contain more than three plies. Further, in FIG. 1, the water resistant composition is applied to the outside surfaces of the product. In other embodiments, the water resistant composition can be applied to other surfaces of the tissue product. For example, the composition can also be applied to internal surfaces contained within the tissue product.

In still further embodiments, it should also be understood that the water resistant composition can be applied to more than two plies. In a specific embodiment, the tissue product is a multi-ply product comprising three or more plies wherein three or more of the plies are treated with the hydrophobic additive. The treated plies are stacked in a manner such that the treated and untreated regions of the nearest adjacent ply containing the hydrophobic additive are offset in the aforementioned manner from the next treated adjacent ply. In this manner a labyrinthial pattern is formed within the product further improving the strikethrough characteristics of the product. In other embodiments, within the labyrinthial pattern, plies not containing the hydrophobic additive are present between one or more of the adjacent treated plies.

For example, in a 5-ply product, in some applications, it may be desirable to apply the water resistant composition to three or more of the plies. The water resistant composition can be applied to the multiple plies in any offset manner from ply to ply. In this embodiment, the water resistant composition can act as a baffle creating a labyrinthine-like fluid flow pattern through the thickness of the product. In a specific embodiment, the hydrophobic composition is applied to the exterior two plies of the 5-ply tissue sheet and the centermost ply such that the untreated areas of the centermost ply are offset from the treated areas of the two exterior plies while the inner plies immediately adjacent to the exterior plies are substantially free from the hydrophobic additive.

In another embodiment the tissue product is a 4-ply tissue product comprising two exterior plies and two interior plies. The two interior plies are treated with the hydrophobic additive and arranged such that the treated and untreated areas of the two interior plies are offset in the aforementioned manner. The exterior two plies of the 4-ply tissue product are substantially free of the hydrophobic additive.

Figure 2:
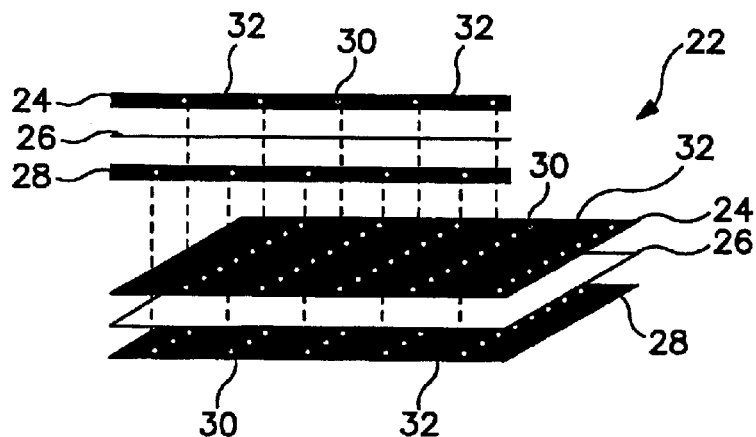
FIG. 2 is a perspective view of another embodiment of a multi-ply tissue product made in accordance with the present invention.

Referring to FIG. 2, another embodiment of a paper product 22 made in accordance with the present invention is shown. Paper product 22 includes a first outer ply 24, a middle ply 26, and a second outer ply 28. In accordance with the present invention, paper product 22 further includes treated areas 32 appearing on opposite sides of the product and untreated areas 30. In this embodiment, the untreated areas 30 appear as round discrete shapes completely surrounded by the water resistant composition. It should be understood, however, that the untreated areas 30 can have any particular shape.

In this embodiment, the untreated areas or pockets 30 are arranged according to a particular pattern. Specifically, the untreated areas 30 appear in regular columns on the surfaces of the paper product. The columns of untreated areas appearing on one side of the paper product are offset in relation to the columns of untreated areas on the opposite side of the paper product.

Figure 3:
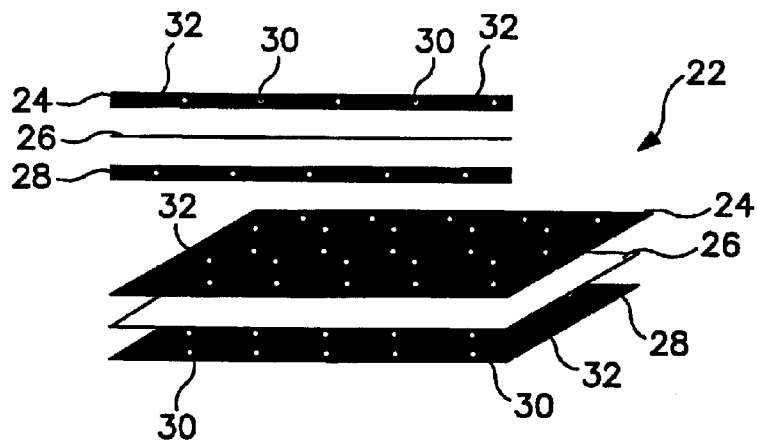
FIG. 3 is a perspective view of another embodiment of a multi-ply tissue product made in accordance with the present invention.

Referring to FIG. 3, another embodiment of a paper product 22 made in accordance with the present invention is shown. Paper product 22 shown in FIG. 3 is very similar in construction to the paper product illustrated in FIG. 2. Consequently, like reference numerals have been used to indicate similar elements.

In contrast to the embodiment illustrated in FIG. 2, however, the untreated areas 30 appearing in FIG. 3 are not arranged in columns on opposite sides of the paper product. Instead, the untreated areas 30 appear randomly dispersed over each side of the product. The untreated areas 30 appearing on ply 24, however, are positioned in an offset relationship with respect to the untreated areas 30 appearing on ply 28.

Referring to FIGS. 4–7, four additional embodiments of paper products 110 treated with a water resistant composition in accordance with the present invention are shown. In FIGS. 4–7, opposite surfaces of the paper products are illustrated. The paper products 110 as shown in FIGS. 4–7 can be single ply products or multi-ply products.

As illustrated, each of the paper products include treated areas 118 and untreated areas 120. In these embodiments, the treated areas 118 appear as stripes or columns. Similarly the untreated areas 120 also generally appear as stripes or columns. As shown, the patterns are generally offset from the top surface of the sheet to the bottom surface of the sheet such that untreated areas on one side of the sheet are aligned with treated areas on the opposite side of the sheet.

Figure 4:
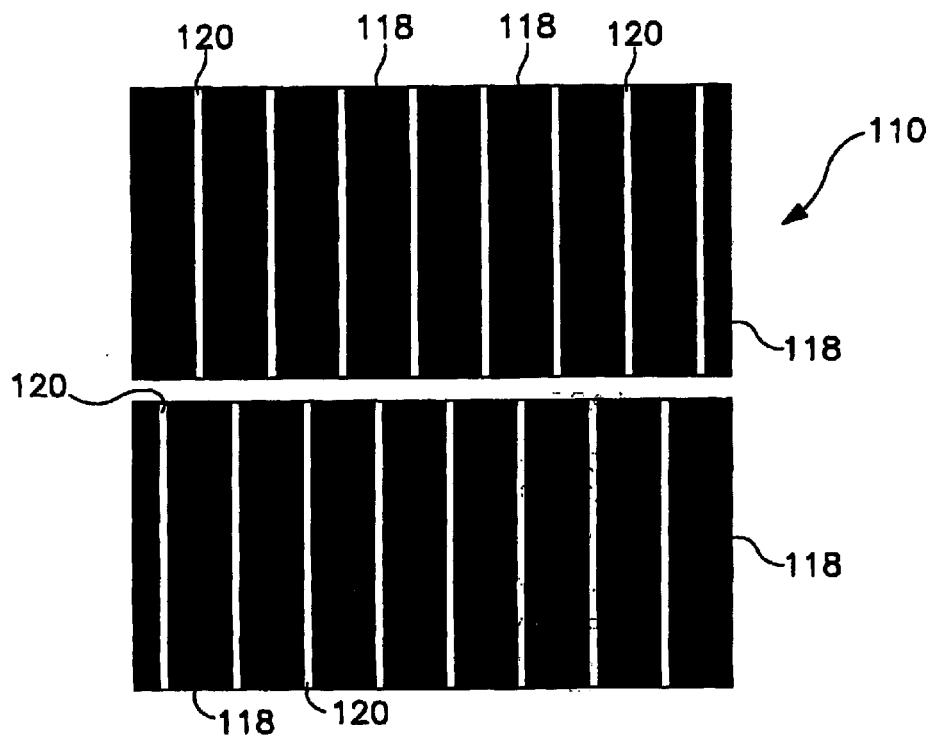
FIG. 4 is a plan view of opposing surfaces of a tissue product made in accordance with the present invention.

Referring particularly to FIG. 4, in this embodiment, the treated areas 118 predominantly cover the surfaces of the paper product. Thin columns of untreated areas 120 separate the treated areas 118.

Figure 5:
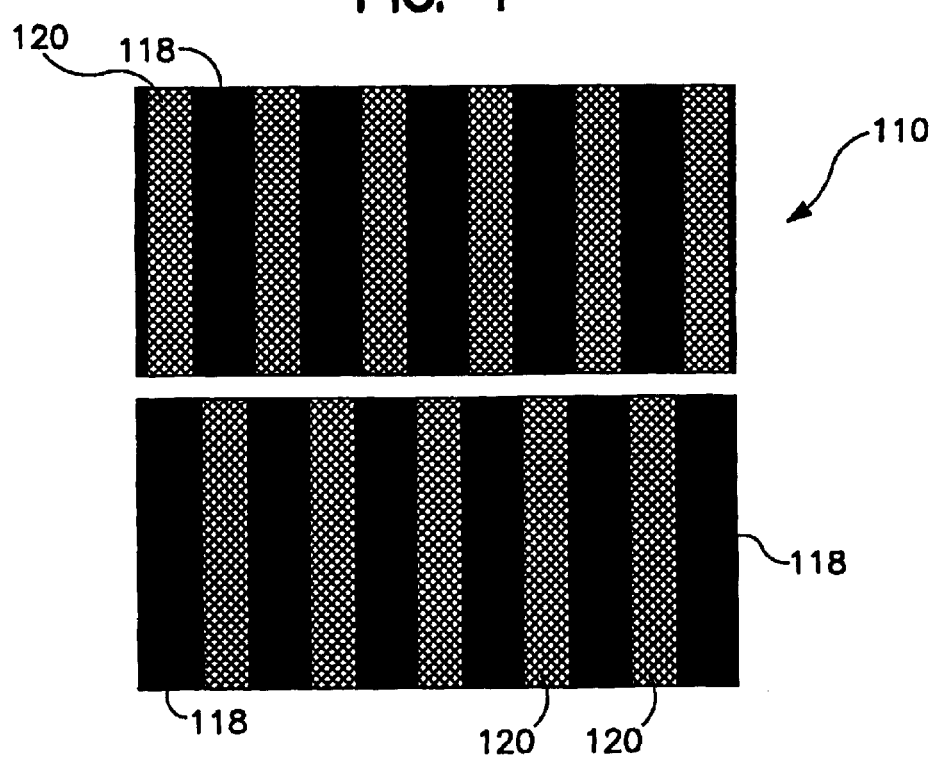
FIG. 5 is a plan view of another embodiment of opposing surfaces of a tissue product made in accordance with the present invention.
Figure 6:
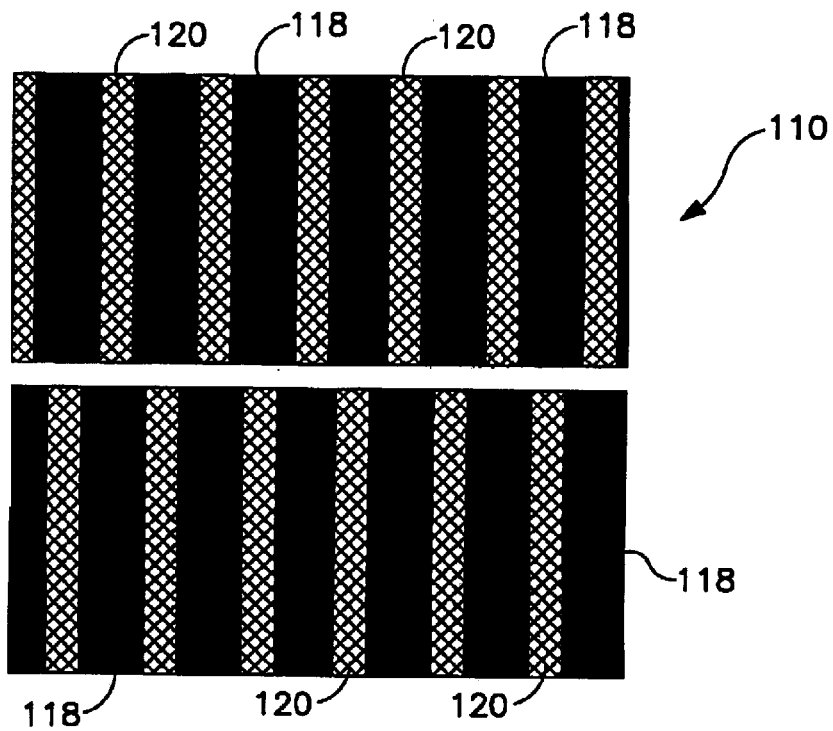
FIG. 6 is a plan view of still another embodiment of opposing surfaces of a tissue product made in accordance with the present invention.
Figure 7:
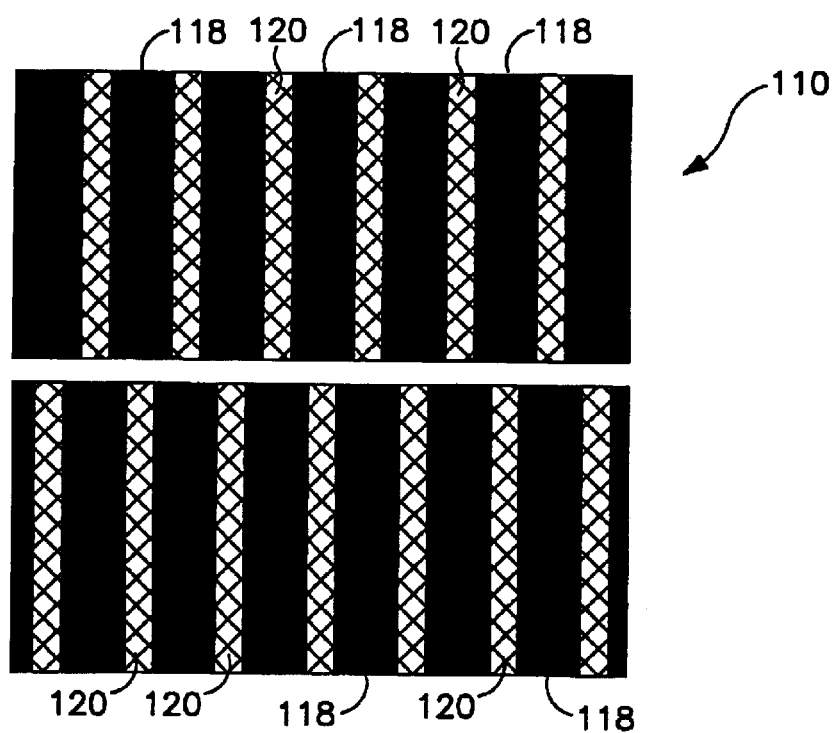
FIG. 7 is a plan view of still another embodiment of opposing surfaces of a tissue product made in accordance with the present invention.

In FIGS. 5–7, the untreated areas 120 generally appear as columns separating treated areas 118. In these embodiments, however, the columns containing the untreated areas 120 further include a pattern of the water resistant composition. In particular, the water resistant composition is applied as a grid to each of the columns in which the untreated areas appear.

Although FIGS. 5–7 all include columns of solid treated areas 118 and columns containing untreated areas 120 in conjunction with a grid of the water resistant composition, particular patterns used in the Figures are varied to show different embodiments of the invention. In particular, the grid appearing in FIG. 5 is more dense than the grids appearing in FIGS. 6 and 7. Further, the column width varies from Figure to Figure. Such variations can be used in order to adjust the properties of the paper product 110. For instance, in some embodiments, it may be more desirable to cover larger surface areas with the water resistant composition than in other embodiments. According to the present invention, these variations can be accomplished by changing the patterns by which the chemical composition is applied, without departing from the scope of the present invention.

In a specific embodiment the hydrophobic additive is applied as stripes or columns aligned with the MD direction of the sheet. In another embodiment the stripes or columns are aligned in the CD direction of the sheet. In still another embodiment the stripes or columns are arranged in a diagonal pattern relative the MD and CD sheet directions.

The manner in which the water resistant composition is applied to paper products in accordance with the present invention is generally not critical. For instance, the water resistant composition can be applied using a rotogravure printer, an inkjet printer, a flexographic printer, a spraying device, and the like. The add-on rate of the water resistant composition (amount applied to the base sheet) can also vary depending upon the particular application. In some applications, the add-on rate can be from about 0.05 percent by weight to about 15 percent by weight of the base sheet, particularly from about 0.2 percent to about 10 percent by weight of the base sheet, and more particularly from about 0.5 percent to about 5 percent by weight of the base sheet.

As described above, paper products made in accordance with the present invention exhibit a beneficial combination of properties. In particular, not only do the products enjoy the benefits of the additives that are applied to the sheets, but the products also maintain acceptable wetability characteristics and strike through characteristics.

Any suitable paper product can be treated in accordance with the present invention. The paper product can be any suitable tissue product, such as a paper towel, a wiper, a bath tissue, a facial tissue or the like. Further, the paper product of the present invention can be generally formed by any of a variety of papermaking processes known in the art. In fact, any process capable of forming a paper web can be utilized in the present invention. For example, a papermaking process of the present invention can utilize adhesive creping, wet creping, double creping, embossing, wet pressing, air pressing, through-air drying, creped through-air drying, uncreped through-air drying, as well as other steps in forming the paper product. Some examples of such techniques are disclosed in U.S. Pat. Nos. 5,048,589 to Cook et al.; U.S. Pat. No. 5,399,412 to Sudall et al.; U.S. Pat. No. 5,129,988 to Farrington et al.; U.S. Pat. No. 5,494,554 to Edwards et al.; which are incorporated herein in the entirety by reference for all purposes.

Also suitable for application of the above mentioned hydrophobic additives are tissue sheets that are pattern densified or imprinted, such as the webs disclosed in any of the following U.S. Pat. Nos. 4,514,345, issued on Apr. 30, 1985, to Johnson et al.; U.S. Pat. No. 4,528,239 issued on Jul. 9, 1985, to Trokhan; U.S. Pat. No. 5,098,522 issued on Mar. 24, 1992; U.S. Pat. No. 5,260,171 issued on Nov. 9,1993, to Smurkoski et al.; U.S. Pat. No. 5,275,700 issued on Jan. 4, 1994, to Trokhan; U.S. Pat. No. 5,328,565 issued on Jul. 12, 1994, to Rasch et al.; U.S. Pat. No. 5,334,289 issued on Aug. 2, 1994, to Trokhan et al.; U.S. Pat. No. 5,431,786 issued on Jul. 11, 1995, to Rasch et al.; U.S. Pat. No. 5,496,624, issued on Mar. 5, 1996, to Steltjes, Jr. et al.; U.S. Pat. No. 5,500,277 issued on Mar. 19, 1996, to Trokhan et al.; U.S. Pat. No. 5,514,523 issued on May 7, 1996, to Trokhan et al.; U.S. Pat. No. 5,554,467 issued on Sep. 10, 1996, to Trokhan et al.; U.S. Pat. No. 5,566,724 issued on Oct. 22, 1996, to Trokhan et al.; U.S. Pat. No. 5,624,790 issued on Apr. 29, 1997, to Trokhan et al.; and, U.S. Pat. No. 5,628,876 issued on May 13, 1997, to Ayers et al., the disclosures of all of which are herein incorporated by reference to the extent that they are non-contradictory herewith. Such imprinted tissue sheets may have a network of densified regions that have been imprinted against a drum dryer by an imprinting fabric, and regions that are relatively less densified (e.g., "domes" in the tissue sheet) corresponding to deflection conduits in the imprinting fabric, wherein the tissue sheet superposed over the deflection conduits is deflected by an air pressure differential across the deflection conduit to form a lower-density pillow-like region or dome in the tissue sheet.

Various drying operations may be useful in the manufacture of the tissue basesheets of the present invention. Examples of such drying methods include, but are not limited to, drum drying, through drying, steam drying such as superheated steam drying, displacement dewatering, Yankee drying, infrared drying, microwave drying, radiofrequency drying in general, and impulse drying, as disclosed in U.S. Pat. No. 5,353,521 issued on Oct. 11, 1994, to Orloff and U.S. Pat. No. 5,598,642 issued on Feb. 4, 1997, to Orloff et al., the disclosures of both which are herein incorporated by reference to the extent that they are non-contradictory herewith. Other drying technologies may be used, such as methods employing differential gas pressure include the use of air presses as disclosed U.S. Pat. No. 6,096,169 issued on Aug. 1, 2000, to Hermans et al. and U.S. Pat. No. 6,143,135 issued on Nov. 7, 2000, to Hada et al., the disclosures of both which are herein incorporated by reference to the extent they are non-contradictory herewith. Also relevant are the paper machines disclosed in U.S. Pat. No. 5,230,776 issued on Jul. 27, 1993, to I. A. Andersson et al.

The paper product treated in accordance with the present invention can also be formed from any suitable fiber furnish. For instance, the paper product can contain softwood fibers, hardwood fibers such as Eucalyptus fibers, and any other papermaking fibers. Further, the furnish can contain smaller amounts of synthetic fibers if desired.

In one embodiment the tissue product comprises hardwood and softwood fibers. The overall ratio of hardwood pulp fibers to softwood pulp fibers within the tissue product, including individual tissue sheets making up the product may vary broadly. The ratio of hardwood pulp fibers to softwood pulp fibers may range from about 9:1 to about 1:9, more specifically from about 9:1 to about 1:4, and most specifically from about 9:1 to about 1:1. In one embodiment of the present invention, the hardwood pulp fibers and softwood pulp fibers may be blended prior to forming the individual plies of the tissue sheet thereby producing a homogenous distribution of hardwood pulp fibers and softwood pulp fibers in the z-direction of the tissue sheet. In another embodiment of the present invention, the hardwood pulp fibers and softwood pulp fibers may be layered so as to give a heterogeneous or stratified distribution of hardwood pulp fibers and softwood pulp fibers in the z-direction of the individual plies of the tissue sheet. In another embodiment, the hardwood pulp fibers may be located in at least one of the outer layers of the tissue product and/or tissue sheets wherein at least one of the inner layers may comprise softwood pulp fibers. In still another embodiment the tissue product contains secondary or recycled fibers optionally containing virgin or synthetic fibers.

In addition, synthetic fibers may also be utilized in the present invention. The discussion herein regarding pulp fibers is understood to include synthetic fibers. Some suitable polymers that may be used to form the synthetic fibers include, but are not limited to: polyolefins, such as, polyethylene, polypropylene, polybutylene, and the like; polyesters, such as polyethylene terephthalate, poly(glycolic acid) (PGA), poly(lactic acid) (PLA), poly($\beta$-malic acid) (PMLA), poly($\epsilon$-caprolactone) (PCL), poly($\rho$-dioxanone) (PDS), poly(3-hydroxybutyrate) (PHB), and the like; and, polyamides, such as nylon and the like. Synthetic or natural cellulosic polymers, including but not limited to: cellulosic esters; cellulosic ethers; cellulosic nitrates; cellulosic acetates; cellulosic acetate butyrates; ethyl cellulose; regenerated celluloses, such as viscose, rayon, and the like; cotton; flax; hemp; and mixtures thereof may be used in the present invention. The synthetic fibers may be located in one or all of the layers and sheets comprising the tissue product.

Additional Chemical Additives

Optional chemical additives may also be added to the aqueous papermaking furnish prior to forming the sheet or to the embryonic tissue sheet to impart additional benefits to the product and process and are not antagonistic to the intended benefits of the present invention. The following materials are included as examples of additional chemicals that may be applied to the tissue sheet along with the hydrophobic additives of the present invention. The chemicals are included as examples and are not intended to limit the scope of the present invention. Such chemicals may be added at any point in the papermaking process including with the hydrophobic additive. They may be blended with the hydrophobic additives of the present invention or as separate additives.

Charge Control Agents

Charge promoters and control agents are commonly used in the papermaking process to control the zeta potential of the papermaking furnish in the wet end of the process. These species may be anionic or cationic, most usually cationic, and may be either naturally occurring materials such as alum or low molecular weight high charge density synthetic polymers typically of molecular weight of about 500,000 or less. Drainage and retention aids may also be added to the furnish to improve formation, drainage and fines retention. Included within the retention and drainage aids are microparticle systems containing high surface area, high anionic charge density materials.

Strength Agents

Wet and dry strength agents may also be applied to the tissue sheet. As used herein, "wet strength agents" refer to materials used to immobilize the bonds between fibers in the wet state. Typically, the means by which fibers are held together in paper and tissue products involve hydrogen bonds and sometimes combinations of hydrogen bonds and covalent and/or ionic bonds. In the present invention, it may be useful to provide a material that will allow bonding of fibers in such a way as to immobilize the fiber-to-fiber bond points and make them resistant to disruption in the wet state. In this instance, the wet state usually will mean when the product is largely saturated with water or other aqueous solutions, but could also mean significant saturation with body fluids such as urine, blood, mucus, menses, runny bowel movement, lymph, and other body exudates.

Any material that when added to a tissue sheet or sheet results in providing the tissue sheet with a mean wet geometric tensile strength:dry geometric tensile strength ratio in excess of about 0.1 will, for purposes of the present invention, be termed a wet strength agent. Typically these materials are termed either as permanent wet strength agents or as "temporary" wet strength agents. For the purposes of differentiating permanent wet strength agents from temporary wet strength agents, the permanent wet strength agents will be defined as those resins which, when incorporated into paper or tissue products, will provide a paper or tissue product that retains more than 50% of its original wet strength after exposure to water for a period of at least five minutes. Temporary wet strength agents are those which show about 50% or less than, of their original wet strength after being saturated with water for five minutes. Both classes of wet strength agents find application in the present invention. The amount of wet strength agent added to the pulp fibers may be at least about 0.1 dry weight percent, more specifically about 0.2 dry weight percent or greater, and still more specifically from about 0.1 to about 3 dry weight percent, based on the dry weight of the fibers.

Permanent wet strength agents will typically provide a more or less long-term wet resilience to the structure of a tissue sheet. In contrast, the temporary wet strength agents will typically provide tissue sheet structures that had low density and high resilience, but would not provide a structure that had long-term resistance to exposure to water or body fluids.

Wet and Temporary Wet Strength Agents

The temporary wet strength agents may be cationic, nonionic or anionic. Such compounds include PAREZ™ 631 NC and PAREZ® 725 temporary wet strength resins that are cationic glyoxylated polyacrylamide available from Cytec Industries (West Paterson, N.J.). This and similar resins are described in U.S. Pat. No. 3,556,932, issued on Jan. 19, 1971 to Coscia et al. and U.S. Pat. No. 3,556,933, issued on Jan. 19, 1971 to Williams et al. Hercobond 1366, manufactured by Hercules, Inc., located at Wilmington, Del., is another commercially available cationic glyoxylated polyacrylamide that may be used in accordance with the present invention. Additional examples of temporary wet strength agents include dialdehyde starches such as Cobond® 1000 from National Starch and Chemical Company and other aldehyde containing polymers such as those described in U.S. Pat. No. 6,224,714 issued on May 1, 2001, to Schroeder et al.; U.S. Pat. No. 6,274,667 issued on Aug. 14, 2001, to Shannon et al.; U.S. Pat. No. 6,287,418 issued on Sep. 11, 2001, to Schroeder et al.; and, U.S. Pat. No. 6,365,667 issued on Apr. 2, 2002, to Shannon et al., the disclosures of which are herein incorporated by reference to the extend they are non-contradictory herewith.

Permanent wet strength agents comprising cationic oligomeric or polymeric resins can be used in the present invention. Polyamide-polyamine-epichlorohydrin type resins such as KYMENE 557H sold by Hercules, Inc., located at Wilmington, Del., are the most widely used permanent wet-strength agents and are suitable for use in the present invention. Such materials have been described in the following U.S. Pat. Nos.: U.S. Pat. No. 3,700,623 issued on Oct. 24, 1972, to Keim; U.S. Pat. No. 3,772,076 issued on Nov. 13, 1973, to Keim; U.S. Pat. No. 3,855,158 issued on Dec. 17, 1974, to Petrovich et al.; U.S. Pat. No. 3,899,388 issued on Aug. 12, 1975, to Petrovich et al.; U.S. Pat. No. 4,129,528 issued on Dec. 12, 1978, to Petrovich et al.; U.S. Pat. No. 4,147,586 issued on Apr. 3, 1979, to Petrovich et al.; and, U.S. Pat. No. 4,222,921 issued on Sep. 16, 1980, to van Eenam. Other cationic resins include polyethylenimine resins and aminoplast resins obtained by reaction of formaldehyde with melamine or urea. It is often advantageous to use both permanent and temporary wet strength resins in the manufacture of tissue products with such use being recognized as falling within the scope of the present invention.

Dry Strength Agents

Dry strength agents may also be applied to the tissue sheet without affecting the performance of the disclosed cationic synthetic co-polymers of the present invention. Such materials used as dry strength agents are well known in the art and include but are not limited to modified starches and other polysaccharides such as cationic, amphoteric, and anionic starches and guar and locust bean gums, modified polyacrylamides, carboxymethylcellulose, sugars, polyvinyl alcohol, chitosans, and the like. Such dry strength agents are typically added to a fiber slurry prior to tissue sheet formation or as part of the creping package. It may at times, however, be beneficial to blend the dry strength agent with the cationic synthetic co-polymers of the present invention and apply the two chemicals simultaneously to the tissue sheet.

Additional Softening Agents

At times it may be advantageous to add additional debonders or softening chemistries to a tissue sheet. Examples of such debonders and softening chemistries are broadly taught in the art. Exemplary compounds include the simple quaternary ammonium salts having the general formula $(R^{1'})_{4-b} N^+ (R^{1''})_b X^-$ wherein R1" is a C1–6 alkyl group, R1" is a C14–C22 alkyl group, b is an integer from 1 to 3 and X– is any suitable counterion. Other similar compounds include the monoester, diester, monoamide and diamide derivatives of the simple quaternary ammonium salts. A number of variations on these quaternary ammonium compounds are known and should be considered to fall within the scope of the present invention. Additional softening compositions include cationic oleyl imidazoline materials such as methyl-1-oleyl amidoethyl-2-oleyl imidazolinium methylsulfate commercially available as Mackernium DC-183 from Mcintyre Ltd., located in University Park, Ill and Prosoft TQ-1003 available from Hercules, Inc.

Miscellaneous Agents

In general, the present invention may be used in conjunction with any known materials and chemicals that are not antagonistic to its intended use. Examples of such materials and chemicals include, but are not limited to, odor control agents, such as odor absorbents, activated carbon fibers and particles, baby powder, baking soda, chelating agents, zeolites, perfumes or other odor-masking agents, cyclodextrin compounds, oxidizers, and the like. Superabsorbent particles, synthetic fibers, or films may also be employed. Additional options include cationic dyes, optical brighteners, absorbency aids and the like. A wide variety of other materials and chemicals known in the art of papermaking and tissue production may be included in the tissue sheets of the present invention including lotions and other materials providing skin health benefits including but not limited to such things as aloe extract and tocopherols such as Vitamin E and the like.

The application point for such materials and chemicals is not particularly relevant to the present invention and such materials and chemicals may be applied at any point in the tissue manufacturing process. This includes pre-treatment of pulp, co-application in the wet end of the process, post treatment after drying but on the tissue machine and topical post treatment.

The basis weight of paper products treated in accordance with the present invention can also vary depending upon the ultimate use for the product. In general, the basis weight can range from about 6 gsm to about 200 gsm and greater. For example, in one embodiment, the paper product can have a basis weight of from about 6 gsm to about 80 gsm.

The present invention may be better understood with respect to the following example.

EXAMPLE

In this example, the following tests were conducted on various tissue sheet samples.

"Wet Out Time" is related to absorbency and is the time is takes for a given sample to completely wet out when placed in water. More specifically, the Wet Out Time is determined by cutting 20 sheets of the paper product into 2.5-inch squares. The number of sheets used in the test is independent of the number of plies per sheet of product. The 20 square sheets are stacked together and stapled at each corner to form a pad. The pad is held close to the surface of a constant temperature distilled water bath (23+/–2° C.), which is the appropriate size and depth to ensure the saturated specimen does not contact the bottom of the container and the top of the surface of the water at the same time. The pad is then dropped flat onto the water surface, staple points down. The time taken for the pad to become completely saturated, measured in seconds, is the Wet Out Time for the sample and represents the absorbent rate of the tissue. Increases in the Wet Out Time represent a decrease in the absorbent rate.

The "Hercules Size Test" (HST) is a test that generally measures how long it takes for a liquid to travel through a tissue sheet. Hercules size testing was done in general accordance with TAPPI method T 530 PM-89, Size Test for Paper with Ink Resistance. Hercules Size Test data was collected on a Model HST tester using white and green calibration tiles and the black disk provided by the manufacturer. A 2% Napthol Green N dye diluted with distilled water to 1% was used as the dye. All materials are available from Hercules, Inc., Wilmington, Del.

All specimens were conditioned for at least 4 hours at 23+/1 1° C. and 50+/−2% relative humidity prior to testing. The test is sensitive to dye solution temperature so the dye solution should also be equilibrated to the controlled condition temperature for a minimum of 4 hours, before testing.

Six tissue sheets (18 plies for a 3-ply product) are selected for testing. Specimens are cut to an approximate dimension of 2.5×2.5 inches. The instrument is standardized with white and green calibration tiles per manufacturer's directions. The specimen (12 plies for a 2-ply product) is placed in the sample holder with the outer surface of the plies facing outward. The specimen is then clamped into the specimen holder. The specimen holder is then positioned in the retaining ring on top of the optical housing. Using the black disk the instrument zero is calibrated. The black disk is removed and 10+/−0.5 milliliters of dye solution is dispensed into the retaining ring and the timer started while placing the black disk back over the specimen. The test time in seconds is recorded from the instrument.

The "Gravimetric Absorbency Test" (GAT) is a test that generally measures the initial absorbency of a tissue sheet. The apparatus and test are well known in the art and are described in U.S. Pat. No. 4,357, 827 which is incorporated herein by reference. In the following example, four tissue sheets (3 plies per sheet; 12 plies total) were tested together. During testing, the sample was placed on a test cell that is in communication with a reservoir vessel. A valve is then opened so that liquid is free to flow from the vessel to the test cell. The sample being tested absorbs liquid from the reservoir vessel. The amount of liquid taken up by the test specimen is determined over a period of time. In particular, the GAT machine generates an absorption curve from one second to as long as desired. In the following examples, the GAT result was obtained by measuring the average slope from between 1 and 4 seconds.

In this example, a 3-ply tissue sheet was treated with a polysiloxane softener in accordance with the present invention and tested for absorbency characteristics according to the above-described tests. For comparison, controls were also tested in which two control samples were completely coated on both sides with the polysiloxane composition (100% surface area coverage). An untreated control sample was also tested.

The tissue sheet tested contained 3 plies and had a bone dry basis weight of 39.2 gsm. Each ply had a bone dry basis weight of 13.1 gsm. Each ply contained 20 percent by weight broke. Each ply was made from a stratified fiber furnish including two outer layers and a middle layer. The first outer layer comprised 40 percent by weight of the ply and contained 100 percent eucalyptus fibers. The middle layer comprised 30 percent by weight of the ply and contained a mixture of softwood fibers, eucalyptus fibers, and broke. The second outer layer also comprised 30 percent by weight of the ply and also contained a mixture of softwood fibers, eucalyptus fibers, and broke. The overall ratio of eucalyptus fibers to softwood fibers was 70 to 30.

The polysiloxane composition that was used to coat the tissue sheet in this example was Y-14344 softener obtained from the Crompton Corporation, Greenwich, Conn.

Sample No. 1

The above described tissue sheet was treated with the above polysiloxane composition in an offset stripe pattern on opposite sides of the sheet according to the present invention. The pattern applied to the sheet is generally shown in FIG. 1. The tissue sheet was coated with the polysiloxane composition according to the following parameters:

Total surface area coverage of each side of the sheet: 60%

Width of treated columns: 2 cm

Width of non-treated columns: 1.33 cm

Amount of offset: 0.33 cm (amount of offset is one-half the difference between the width of the treated columns and the width of the non-treated columns)

Add on rate: 1.02 percent by weight

Sample No. 2

Sample No. 2 was treated similar to Sample No. 1 according to the following parameters:

Total surface area coverage of each side of the sheet: 90%

Width of treated columns: 2 cm

Width of non-treated columns: 0.22 cm

Amount of offset: 0.89 cm (amount of offset is one-half the difference between the width of the treated columns and the width of the non-treated columns)

Add on rate: 2.83 percent by weight

Sample No. 3

Sample No. 3 was treated with the polysiloxane composition so as to form treated columns and untreated columns. The untreated columns, in this sample, contained a crosshatch pattern as shown in FIG. 5. The treated sheet had the following parameters:

Total surface area coverage of each side of the sheet: 90%

Width of treated columns: 2 cm

Width of non-treated columns: 0.40 cm

Pattern line diameter: 0.5 mm

Crosshatch repeat: 2.8 mm by 3.8 mm

Total crosshatch density: 40%

Amount of offset: 0.80 cm (amount of offset is one-half the difference between the width of the treated columns and the width of the non-treated columns)

Add on rate: 2.83 percent by weight

Control Samples No. 1 and No. 2

Control samples were also produced in which each side of the tissue sheet was completely coated with the polysiloxane composition. The add on rate of the polysiloxane composition was 2.89 percent by weight for both samples.

Control Sample No. 3

Another control sample was also tested that was not treated with the polysiloxane composition.

The following results were obtained:

TABLE 1

| Sample No | HST (S) | Wet Out Time (S) | GAT (g/g/s) |
| --- | --- | --- | --- |
| 1 | 0.6 | 8.9 | 0.25 |
| 2 | 1.2 | 14.2 | 0.17 |
| 3 | 1.5 | 11.2 | 0.12 |
| Control 1 (coated) | 4.0 | 16.8 | 0.14 |
| Control 2 (coated) | 6.9 | 16.6 | 0.10 |
| Control 3 (untreated) | 0.5 | 3.3 | 0.44 |

In order to test the stability of the above treated tissue sheets, the HST test was repeated after the samples had been stored for four weeks. Specifically, subsets of each of the above polysiloxane treated samples were stored for four weeks at 73° F., at 100° F., and at 130° F.

The following results were obtained:

TABLE 2

| Sample No. | HST Initial (S) | HST after 4 wks. @ 73° F. (S) | HST after 4 wks. @ 100° F. (S) | HST after 4 wks.@ 130° F. (S) |
|---|---|---|---|---|
| 1 | 0.6 | 0.7 | 0.8 | 0.9 |
| 2 | 1.2 | 1.6 | 2.5 | 4.6 |
| 3 | 1.5 | 2.3 | 6.8 | 19.3 |
| Control 1 (coated) | 4.0 | 10.7 | 34.5 | 88.1 |
| Control 2 (coated) | 6.9 | 11.8 | 37.7 | >120 |

As shown above, samples treated in accordance with the present invention were much more stable than the control samples which were completely coated on each side with the polysiloxane composition.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A paper product comprising:
a paper sheet having a first side and a second side, the paper sheet having a bulk density of at least about 2 g/cc, the paper sheet containing pulp fibers; and
a water resistant chemical additive applied to the first side of the paper sheet according to a first pattern and applied to the second side of the paper sheet according to a second pattern, the water resistant chemical additive comprising a material selected from the group consisting of a softener, a lotion, a skin-conditioning agent, a sunscreen agent, an anti-acne agent, an antimicrobial agent, a cosmetic astringent, an emollient, an anti-friction agent, a debonder, an antifungal agent, a sizing agent, an antiseptic agent, a drug astringent, an external analgesics, a skin exfoliating agent, a skin protectant, and mixtures thereof, the first pattern covering from about 50% to about 99% of the surface area of the first side of the sheet and the second pattern covering from about 50% to about 99% of the surface area of the second side of the sheet, each of the patterns including non-treated areas and treated areas, and wherein the patterns are applied to the sheet in an offset relationship such that the non-treated areas applied to one side of the sheet are located opposite treated areas on the other side of the sheet.

2. A paper product as defined in claim 1, wherein the paper product is a bath tissue or a facial tissue.

3. A tissue product as defined in claim 2, wherein the paper sheet comprises a stratified web having 2 outer layers of fibers and a middle layer of fibers, the outer layers comprising hardwood fibers, while the middle layer comprising softwood fibers.

4. A paper product as defined in claim 1, wherein the paper product is a paper towel.

5. A paper product as defined in claim 1, wherein the treated areas and the untreated areas form alternating columns on each side of the paper sheet.

6. A paper product as defined in claim 1, wherein the untreated areas comprise pockets surrounded on all sides by the treated areas.

7. A paper product as defined in claim 6, wherein the pockets are arranged in columns.

8. A paper product as defined in claim 1, wherein the first and second patterns comprise alternating stripes, a first set of the stripes comprising columns completely covered by the chemical additive, and a second set of the stripes comprising columns having treated areas and non-treated areas, the treated areas within the second set of stripes forming a grid.

9. A paper product as defined in claim 1, wherein the water resistant chemical additive comprises a hydrophobic additive.

10. A paper product as defined in claim 9, wherein the water resistant chemical additive comprises a surface-sizing agent.

11. A paper product as defined in claim 9, wherein the hydrophobic additive comprises a polysiloxane.

12. A paper product of claim 11, wherein the hydrophobic additive comprises an amino functional polysiloxane.

13. A product of claim 12, wherein the amino functional polysiloxane comprises:

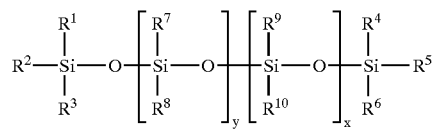

wherein x and y are integers >0;
the mole ratio of x to (x+y) is from about 0.005 percent to about 25 percent;
$R^1$–$R^9$ are independently any $C_1$ or higher alkyl groups; and
$R^{10}$ moiety is an amino functional moiety containing one or more secondary amine, tertiary amine, quaternary amine, or unsubstituted amide group and mixtures thereof.

14. A paper product as defined in claim 1, wherein the water resistant chemical additive covers from about 75% to about 99% of the surface area of both sides of the sheet.

15. A paper product as defined in claim 14, wherein the paper sheet comprises at least 3 plies.

16. A paper product as defined in claim 15, wherein the paper product comprises a facial tissue, the paper sheet having a basis weight of from about 10 gsm to about 60 gsm.

17. A paper product as defined in claim 1, wherein the paper sheet comprises a plurality of plies.

18. A paper product as defined in claim 17, wherein the tissue product is a multi-ply tissue product comprising three or more plies wherein the inner plies are substantially free of the water resistant chemical additive.

19. A paper product as defined in claim 17, wherein the tissue product is a multi-ply product comprising three or more plies wherein three or more of the plies are treated with the water resistant chemical additive; the treated plies are arranged in a manner such that the treated and untreated regions of the nearest adjacent treated ply or plies are arranged in an offset relationship such that the non-treated areas of a treated ply are located opposite treated areas on the nearest adjacent treated ply or plies.

20. A paper product of claim 19, wherein the tissue product is a 5-ply tissue sheet wherein the water resistant chemical additive is applied to the exterior two plies of the 5-ply tissue sheet and the centermost ply of the 5-ply tissue sheet such that the untreated areas of the centermost ply are offset from the treated areas of the two exterior plies while the inner plies immediately adjacent to the exterior plies are substantially free of the water resistant chemical additive.

21. A paper product of claim 17, wherein the paper product is a 4-ply tissue product comprising two exterior plies and two interior plies; the two interior plies of the tissue product are treated with the water resistant chemical additive and arranged such that the patterns of the two treated plies are arranged in an offset relationship such that the non-treated areas applied to the first treated ply are located opposite the treated areas of the second treated ply and wherein the exterior two plies of the 4-ply tissue product are substantially free of the water resistant chemical additive.

22. A paper product as defined in claim 1, wherein the water resistant chemical additive has been applied by a gravure printer.

23. A paper product as defined in claim 1, wherein the water resistant chemical additive has been applied by an inkjet printer.

24. A paper product as defined in claim 1, wherein the water resistant chemical additive has been applied by a flexographic printer.

25. A paper product comprising:
a paper sheet comprising a plurality of plies, the paper sheet containing a first surface and a second surface, the paper sheet containing pulp fibers;
a water resistant chemical additive applied to the first surface of the paper sheet according to a first pattern and applied to the second surface of the paper sheet according to a second pattern, the first pattern covering from about 50% to about 99% of the surface area of the first surface and the second pattern covering from about 50% to about 99% of the surface area of the second surface, each of the patterns including non-treated areas and treated areas, and wherein the patterns are applied to the surfaces in an offset relationship such that the non-treated areas applied to one surface are located opposite the treated areas on the other surface.

26. A paper product as defined in claim 25, wherein the paper product is a bath tissue or a facial tissue.

27. A paper product as defined in claim 25, wherein the paper product is a paper towel.

28. A paper product as defined in claim 25, wherein the treated areas and the untreated areas form alternating columns on each surface.

29. A paper product as defined in claim 25, wherein the untreated areas comprise pockets surrounded on all sides by the treated areas.

30. A paper product as defined in claim 25, wherein the first and second patterns comprise alternating stripes, a first set of the stripes comprising columns completely covered by the water resistant chemical additive, and a second set of the stripes comprising columns having treated areas and non-treated areas, the treated areas within the second set of stripes forming a grid.

31. A paper product as defined in claim 25, wherein the water resistant chemical additive comprises a hydrophobic additive.

32. A paper product as defined in claim 31, wherein the water resistant chemical additive comprises a surface-sizing agent.

33. A paper product as defined in claim 31, wherein the hydrophobic additive comprises a polysiloxane.

34. A paper product of claim 33, wherein the hydrophobic additive comprises an amino functional polysiloxane.

35. A paper product of claim 34, wherein the amino functional polysiloxane comprises:

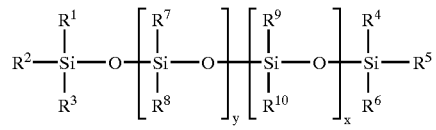

wherein x and y are integers >0;
the mole ratio of x to (x+y) is from about 0.005 percent to about 25 percent:
$R^1$–$R^9$ are independently any $C_1$ or higher alkyl groups; and
$R^{10}$ moiety is an amino functional moiety containing one or more secondary amine, tertiary amine, quaternary amine, or unsubstituted amide group and mixtures thereof.

36. A paper product as defined in claim 25, wherein the water resistant chemical additive covers from about 75% to about 99% of the surface area of both surfaces.

37. A paper product as defined in claim 25, wherein the paper sheet comprises 3-plies.

38. A paper product as defined in claim 25, wherein the paper sheet has a basis weight of from about 6 gsm to about 80 gsm.

39. A paper product as defined in claim 25, wherein the first surface and the second surface are exterior surfaces of the paper sheet.

40. A paper product as defined in claim 25, wherein at least the first surface or the second surface comprises an internal surface contained within the paper sheet.

41. A paper product as defined in claim 25, wherein the first surface and the second surface comprise internal surfaces of the paper sheet.

42. A tissue product comprising:
a tissue sheet having a first side and a second side, the tissue sheet having a bulk density of at least about 2 cc/g, the tissue sheet having a basis weight of from about 6 gsm to about 35 gsm, the tissue sheet comprising at least 3-plies, the tissue sheet being made from pulp fibers;
a hydrophobic additive applied to the first side of the tissue sheet according to a first pattern and applied to the second side of the tissue sheet according to a second pattern, the hydrophobic additive comprising a softener, the first pattern covering from about 75% to about 99% of the surface area of the first side of the sheet and the second pattern covering from about 75% to about 99% of the surface area of the second side of the sheet, each of the patterns including non-treated areas and treated areas, and wherein the patterns are applied to the tissue sheet in an offset relationship such that the non-treated areas appearing on one side of the tissue sheet are located opposite treated areas on the other side of the tissue sheet.

43. A tissue product as defined in claim 42, wherein the treated areas and the untreated areas form alternating columns on each side of the tissue sheet.

44. A tissue product as defined in claim 42, wherein the untreated areas comprise pockets surrounded on all sides by the treated areas.

45. A tissue product as defined in claim 42, wherein the first and second patterns comprise alternating stripes, a first set of the stripes comprising columns completely covered by the hydrophobic additive, and a second set of the stripes comprising columns having treated areas and non-treated areas, the treated areas within the second set of stripes forming a grid.

46. A tissue product as defined in claim 42, wherein the outer plies of the tissue sheet comprise stratified paper webs, the paper webs having two outer layers comprising hardwood fibers and a middle layer comprising softwood fibers.

47. A process for making a tissue product having improved strikethrough and absorbent properties, said process comprising the steps of supplying a tissue sheet having a bulk of greater than about 2 cm$^2$/g and comprising one or more plies and treating said tissue sheet with a water resistant chemical additive such that the water resistant chemical additive is applied to the first side of the paper sheet according to a first pattern and applied to the second side of the paper sheet according to a second pattern, the water resistant chemical additive comprising a material selected from the group consisting of a softener, a lotion, a skin-conditioning agent, a sunscreen agent, an anti-acne agent, an anti-microbial agent, a cosmetic astringent, an emollient, an anti-friction agent, a debonder, an antifungal agent, a sizing agent, an antiseptic agent, a drug astringent, an external analgesics, a skin exfoliating agent, a skin protectant, and mixtures thereof the first pattern covering from about 50% to about 99% of the surface area of the first side of the sheet and the second pattern covering from about 50% to about 99% of the surface area of the second side of the sheet, each of the patterns including non-treated areas and treated areas, and wherein the patterns are applied to the sheet in an offset relationship such that the non-treated areas applied to one side of the sheet are located opposite treated areas on the other side of the sheet.

48. The process of claim 47, wherein the paper product is a bath tissue or a facial tissue.

49. The process of claim 48, wherein the paper product is a paper towel.

50. The process of claim 48, wherein the treated areas and the untreated areas form alternating columns on each side of the paper sheet.

51. The process of claim 48, wherein the untreated areas comprise pockets surrounded on all sides by the treated areas.

52. The process of claim 51, wherein the pockets are arranged in columns.

53. The process of claim 47, wherein the first and second patterns comprise alternating stripes, a first set of the stripes comprising columns completely covered by the chemical additive, and a second set of the stripes comprising columns having treated areas and non-treated areas, the treated areas within the second set of stripes forming a grid.

54. The process of claim 47, wherein the water resistant chemical additive comprises a hydrophobic additive.

55. The process of claim 54, wherein the water resistant chemical additive comprises a surface sizing agent.

56. The process of claim 54, wherein the hydrophobic additive comprises a polysiloxane.

57. The process of claim 56, wherein the hydrophobic additive comprises an amino functional polysiloxane.

58. The process of claim 57, wherein the amino functional polysiloxane comprises:

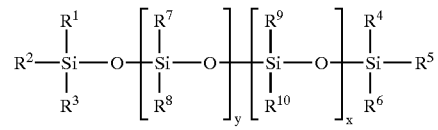

wherein x and y are integers >0;

the mole ratio of x to (x+y) is from about 0.005 percent to about 25 percent;

$R^1$–$R^9$ are independently any $C_1$ or higher alkyl groups; and $R^{10}$ moiety is an amino functional moiety containing one or more secondary amine, tertiary amine, quaternary amine, or unsubstituted amide group and mixtures thereof.

59. The process of claim 47, wherein the water resistant chemical additive covers from about 75% to about 99% of the surface area of both sides of the sheet.

60. The process of claim 47, wherein the paper sheet comprises a plurality of plies.

61. The process of claim 47, wherein the tissue product is a multi-ply tissue product comprising three or more plies wherein the inner plies are substantially free of the water resistant chemical additive.

62. A process of making a multi-ply tissue product of 3 or more plies having improved strikethrough and absorbent properties, said process comprising the steps of 1) supplying multiple plies of a first tissue sheet having a bulk of greater than about 2 cm$^2$/g, said tissue sheet being treated with a water resistant chemical additive such that from about 50% to about 99% of the surface area of the sheet is treated with the water resistant chemical such that the sheet contains treated and untreated areas and 2) arranging the plies in a manner such the treated and untreated regions of the nearest adjacent treated ply or plies are arranged in an offset relationship such that the non-treated areas of a treated ply are located opposite treated areas on the nearest adjacent treated ply or plies.

63. The process of claim 62 further comprising the step of supplying additional untreated plies to the tissue product, said untreated plies being substantially free of the water resistant chemical additive and arranging said untreated plies to lie between two or more of the adjacent treated plies.

* * * * *

UNITED STATES PATENT AND TRADEMARK OFFICE
CERTIFICATE OF CORRECTION

PATENT NO. : 6,896,766 B2
DATED : May 24, 2005
INVENTOR(S) : Benjamin Sarbo et al.

Page 1 of 1

It is certified that error appears in the above-identified patent and that said Letters Patent is hereby corrected as shown below:

Column 21,
Line 21, "mixtures thereof the" should read -- mixtures thereof, the --.

Signed and Sealed this

Twenty-fifth Day of April, 2006

JON W. DUDAS
*Director of the United States Patent and Trademark Office*